(12) United States Patent
Louis et al.

(10) Patent No.: US 8,557,871 B2
(45) Date of Patent: Oct. 15, 2013

(54) DERMATOLOGICAL COMPOSITIONS COMPRISING RETINOIDS, DISPERSED BENZOYL PEROXIDE AND CARRAGEENANS

(75) Inventors: Fabienne Louis, Villeneuve-Loubet (FR); Sandrine Segura, Biot (FR); Nathalie Willcox, Magagnosc (FR)

(73) Assignee: Galderma Research & Development, Biot (FR)

( * ) Notice: Subject to any disclaimer, the term of this patent is extended or adjusted under 35 U.S.C. 154(b) by 346 days.

(21) Appl. No.: 12/833,335

(22) Filed: Jul. 9, 2010

(65) Prior Publication Data

US 2011/0003894 A1 Jan. 6, 2011

Related U.S. Application Data

(63) Continuation of application No. PCT/FR2009/050040, filed on Jan. 12, 2009.

(30) Foreign Application Priority Data

Jan. 10, 2008 (FR) ...................................... 08 50131

(51) Int. Cl.
  *A61K 31/19* (2006.01)
  *A61K 31/075* (2006.01)
  *A61K 47/00* (2006.01)

(52) U.S. Cl.
  USPC ............ 514/569; 514/714; 514/782; 424/401

(58) Field of Classification Search
  USPC .......................... 514/569, 714, 78; 424/401
  See application file for complete search history.

(56) References Cited

U.S. PATENT DOCUMENTS

| 6,010,706 A * | 1/2000 | Candau et al. ............... 424/401 |
| 6,322,798 B1 | 11/2001 | Candau |
| 7,820,186 B2 * | 10/2010 | Orsoni et al. ................ 424/401 |
| 7,964,202 B2 * | 6/2011 | Orsoni et al. ................ 424/401 |
| 8,105,618 B2 * | 1/2012 | Orsoni-Segona et al. .... 424/401 |
| 8,241,649 B2 * | 8/2012 | Orsoni et al. ................ 424/401 |
| 2003/0170196 A1 | 9/2003 | Orsoni et al. |

FOREIGN PATENT DOCUMENTS

| FR | 2718018 A1 | 10/1995 |
| WO | WO 2007/092312 A2 | 8/2007 |
| WO | WO 2008/087354 A2 | 7/2008 |

* cited by examiner

*Primary Examiner* — Sreeni Padmanabhan
*Assistant Examiner* — Jody Karol
(74) *Attorney, Agent, or Firm* — Dentons US LLP

(57) ABSTRACT

Dermatological compositions containing, in a physiologically acceptable medium, at least one retinoid, dispersed benzoyl peroxide and at least one gelling agent of the family of the carrageenans, are useful for treating dermatological conditions and afflictions linked to disorders of cell differentiation and/or proliferation and/or keratinization, notably for treating acne vulgaris.

46 Claims, No Drawings

DERMATOLOGICAL COMPOSITIONS COMPRISING RETINOIDS, DISPERSED BENZOYL PEROXIDE AND CARRAGEENANS

CROSS-REFERENCE EARLIER APPLICATIONS

This application is a continuation of PCT/FR 2009/050040, filed Jan. 12, 2009 and designating the United States (published in the French language on Jul. 30, 2009 as WO 2009/092954 A1; the title and abstract were also published in English), which claims priority under 35 U.S.C. §119 of FR 0850131, filed Jan. 10, 2008, each hereby expressly incorporated by reference in its entirety and each assigned to the assignee hereof.

BACKGROUND OF THE INVENTION

1. Technical Field of the Invention

The present invention relates to dermatological compositions comprising, formulated into a physiologically acceptable medium, at least one retinoid, dispersed benzoyl peroxide and at least one carrageenan.

2. Description of Background and/or Related and/or Prior Art

The administration of several categories of active principles is a therapeutic tool to which recourse is frequently had, in particular in the treatment of dermatological disorders.

Specifically, it is known to administer peroxides, vitamins D and retinoids in the topical treatment of various pathologies related to the skin or mucous membranes, in particular acne.

The combination of several local treatments (antibiotics, retinoids, peroxides, zinc) is also employed in dermatology to make it possible to enhance the effectiveness of the active principles and to reduce their toxicity (Cunliffe W. J., J. Dermatol. Treat., 2000, 11 (Suppl. 2), S13-S14).

The multiple application of different dermatological products may be rather burdensome and demanding for the patient.

The interest in attempting to obtain a novel treatment which is effective with regard to dermatological conditions in a stable composition which offers a good cosmetic quality, which makes possible a single application and which makes possible administration which is agreeable to the patient is thus understood.

There is nothing among this range of therapies provided to one skilled in the art which would encourage him to combine, in the same composition, benzoyl peroxide, a retinoid and several gelling agents.

This is because the formulation of such a composition presents several problems.

First of all, the effectiveness of the benzoyl peroxide is related to its decomposition when it is brought into contact with the skin. This is because it is the oxidizing properties of the free radicals produced during this decomposition which result in the desired effect. Consequently, to maintain the optimum effectiveness of the benzoyl peroxide, it is important to prevent it from decomposing before use, that is to say during storage. In point of fact, benzoyl peroxide is an unstable chemical compound, which makes it difficult to formulate it into finished products.

The solubility and the stability of benzoyl peroxide have been studied by Chellquist et al. in ethanol, propylene glycol and various mixtures of polyethylene glycol 400 (PEG 400) and water (Chellquist E. M. and Gorman W. G., Pharm. Res., 1992, Vol. 9, 1341-1346). It turns out that benzoyl peroxide is particularly soluble in PEG 400 and ethanol.

This document furthermore specifies that the stability of benzoyl peroxide is strongly influenced by the chemical composition of the formulation and by the storage temperature. Benzoyl peroxide is highly reactive and decomposes in solution at low temperature due to the instability of its peroxide bond.

The authors thus determine that benzoyl peroxide in solution decomposes more or less rapidly in all the solvents studied according to the type of solvent and its concentration.

The decomposition times of benzoyl peroxide in PEG 400 (0.5 mg/g), in ethanol and in propylene glycol are 1.4, 29 and 53 days respectively at 40° C. Such a decomposition does not make possible the formulation of a product intended for sale.

Furthermore, it is known that benzoyl peroxide is more stable in water and propylene glycol when it is in suspension (i.e., in the dispersed form), since it is not decomposed after storing for 90 days in these solvents.

Thus, to limit the problem of rapid instability of benzoyl peroxide in solution, it has proven to be advantageous to formulate benzoyl peroxide in the dispersed form.

However, this type of formulation is not completely satisfactory insofar as the benzoyl peroxide is still found to be decomposed in the finished product.

Another difficulty to be overcome in the formulation of a composition comprising both benzoyl peroxide and a retinoid is that the majority of retinoids are particularly sensitive to natural oxidation, to visible light and ultraviolet radiation. As benzoyl peroxide is a strong oxidizing agent, the chemical compatibility of these two compounds in one and the same formulation presents numerous problems of stability from the physical and chemical viewpoint.

A stability study was carried out on two retinoids by combining two commercial products, one comprising a retinoid (tretinoin or adapalene) and the second based on benzoyl peroxide (B. Martin et al., Br. J. Dermatol., (1998) 139, (suppl. 52), 8-11).

The presence of benzoyl peroxide in the formulation causes very rapid decomposition of the oxidation-sensitive retinoids: 50% of the tretinoin is measured as decomposing in 2 hours and 95% in 24 hours. In the composition comprising adapalene as retinoid, no decomposition of the adapalene was measured during 24 hours.

This study confirms that benzoyl peroxide is decomposed and decomposes oxidation-sensitive retinoids over time by gradually releasing benzoic acid in finished products.

In point of fact, it is clear that the decomposition of benzoyl peroxide and retinoids is not desirable insofar as it is harmful to the effectiveness of the composition in which they are present.

Nothing thus prompted the combining of these two active agents to obtain a stable composition of gel or emulsion type, it being known that it was conventionally recognized that the presence of benzoyl peroxide chemically and physically destabilized compositions of these types.

In particular, the formulation as a gel of benzoyl peroxide and a retinoid is advantageous for topical treatments, such as that of acne, as it avoids in particular leaving a greasy feel remaining on the skin.

More specifically, the term "gel" means a system comprising at least one thermodynamically stable phase (in general one or two phases) resulting from the coagulation as a three-dimensional network of a colloidal solution. More precisely, an aqueous gel corresponds to a composition comprising, in an aqueous phase, a viscoelastic mass formed from colloidal suspensions (carrageenan or combination of a carrageenan with another gelling agent).

In particular, the formulation as a "light" emulsion of benzoyl peroxide and a retinoid is advantageous for topical treatments, such as that of acne, as, in the case of a "light" emulsion, it contributes emollience while avoiding leaving an excessively greasy feel remaining on the skin.

"Light" emulsion means an emulsion comprising a low proportion of fatty phase, the aqueous phase remaining predominant. An emulsion is a system comprising two fluids which are insoluble or only slightly soluble in one another, and in which one of the fluids is dispersed in the other as microscopic particles. Preferably, the emulsions used comprise or do not comprise at least one emulsifier, a polar hydrophilic phase, preferably aqueous phase, and a nonpolar fatty phase. Preferably, they are provided in the form of "oil-in-water" (O/W) or "water-in-oil" (W/O) emulsions.

In point of fact, another difficulty to be overcome in the formulation of a composition comprising in particular benzoyl peroxide, when it occurs in the gel or emulsion form, is that the gelling agents of the aqueous phase are destabilized by the benzoic acid released during the decomposition of the benzoyl peroxide.

Specifically, the gelling agents of the aqueous phase most commonly used with benzoyl peroxide are acrylic acid polymers (carbomer).

In point of fact, the use of carbomers in compositions of aqueous gel type does not provide good results in terms of chemical stability of the benzoyl peroxide and in terms of rheological stability. As described by Bollinger (Bollinger, Journal of Pharmaceutical Science, 1977, Vol. 5), a loss of 5 to 20% of benzoyl peroxide after 2 months at 40° C., depending on the neutralizing agent of the carbomer used, was observed. Furthermore, the release of benzoic acid brings about depolymerization of the carbomers, giving a fall in viscosity which may bring about phase separation.

This instability of benzoyl peroxide gels (as such or as gelled aqueous phase of an emulsion) is thus harmful to their effectiveness and to their cosmetic quality.

Furthermore, a finished product, in particular when it concerns pharmaceutical or cosmetic compositions, must maintain, throughout its lifetime, precise physicochemical criteria which make it possible to guarantee its pharmaceutical and cosmetic quality. Among these criteria, it is necessary for the rheological properties to be retained. They define the behavior and the texture of the composition during application but also the properties of release of the active principle [SFSTP Commission report 1998] and the homogeneity of the product when the active principles are present therein in the dispersed state.

Need thus exists for a physically and chemically stable composition of gel or emulsion type comprising benzoyl peroxide and a retinoid.

SUMMARY OF THE INVENTION

Dermatological compositions of gel and emulsion type have now been developed which meet this need, which comprise dispersed benzoyl peroxide in the free or encapsulated form, at least one retinoid and at least one carrageenan, which have good physical stability, that is to say which do not exhibit a drop in viscosity over time and in particular at ambient temperature, and which maintain good chemical stability of the two active principles (benzoyl peroxide and retinoid). In particular, decomposition of the active principles over time and/or at ambient temperature is not observed.

The present invention thus features compositions comprising, formulated into the same physiologically acceptable medium:
at least one retinoid,
benzoyl peroxide,
at least one gelling agent of the family of the carrageenans, the said benzoyl peroxide and/or the said at least one retinoid preferably being in a form dispersed in the said composition.

DETAILED DESCRIPTION OF BEST MODE AND SPECIFIC/PREFERRED EMBODIMENTS OF THE INVENTION

According to a preferred embodiment, the composition is a combination, the active principles of which are combined at fixed doses within one and the same vehicle (single formulation) which delivers them together. Preferably, the pharmaceutical composition in the form of a fixed combination is a gel; in this case, the two active principles are dispersed and intimately mixed during formulation in one and the same vehicle, which delivers them together when the gel is applied.

The term "physiologically acceptable medium" means a medium compatible with the skin, mucous membranes and superficial body growths.

Preferably, the pharmaceutical composition is useful for a single topical application daily.

The term "active principle in the dispersed form according to the invention" means an active principle in the form of solid particles suspended in a given vehicle. Such particles have in particular a size of greater than 10 μm.

Advantageously, the particle size of the retinoid and of the benzoyl peroxide is such that at least 80% by number of the particles and preferably at least 90% by number of the particles have a diameter of less than 25 μm and at least 99% by number of the particles have a diameter of less than 100 μm.

The compositions according to the invention comprise at least one retinoid. The term "retinoid" means any compound which binds to RAR and/or RXR receptors. Preferably, the retinoid is a compound selected from the family of the benzonaphthalene retinoids (also known as naphthoic acid compounds), such as described in EP-0199636, in particular:
6-(3-methylphenyl)-2-naphthoic acid and its methyl ester,
6-(4-(tert-butyl)phenyl)-2-naphthoic acid and its methyl ester,
6-(3-(tert-butyl)phenyl)-2-naphthoic acid and its methyl ester,
6-(3,4-dimethoxyphenyl)-2-naphthoic acid and its methyl ester,
6-(p-(1-adamantylthio)phenyl)-2-naphthoic acid and its methyl ester,
6-(3-(1-adamantyl)-4-methoxyphenyl)-2-naphthoic acid (adapalene) and its methyl ester,
the methyl ester of 6-[3-(1-adamantyl)-4-(tert-butyldimethylsilyloxy)phenyl]-2-naphthoic acid,
the methyl ester of 6-[3-(1-adamantyl)-4-hydroxyphenyl]-2-naphthoic acid,
6-[3-(1-adamantyl)-4-hydroxyphenyl]-2-naphthoic acid,
the methyl ester of 6-[3-(1-adamantyl)-4-decyloxyphenyl]-2-naphthoic acid,
6-[3-(1-adamantyl)-4-decyloxyphenyl]-2-naphthoic acid,
the methyl ester of 6-[3-(1-adamantyl)-4-hexyloxyphenyl]-2-naphthoic acid,
6-[3-(1-adamantyl)-4-hexyloxyphenyl]-2-naphthoic acid,
the methyl ester of 6-[3-(1-adamantyl)-4-methoxyphenyl]-4-acetoxy-1-methyl-2-naphthoic acid,
6-[3-(1-adamantyl)-4-methoxyphenyl]-4-hydroxy-1-methyl-2-naphthoic acid, the methyl ester of 6-[3-(1-adamantyl)-4-methoxyphenyl]-4-hydroxy-1-methyl-2-naphthoic acid,
the methyl ester of 6-[3-(1-adamantyl)-4-methoxyphenyl)-1-methyl-2-naphthoic acid,
6-[3-(1-adamantyl)-4-methoxyphenyl]-1-methyl-2-naphthoic acid,
6-[3-(1-adamantyl)-4-methoxyphenyl]-2-naphthalenemethanol,
the ethyl amide of 6-[3-(1-adamantyl)-4-methoxyphenyl]-2-naphthoic acid,
the morpholide of 6-[3-(1-adamantyl)-4-methoxyphenyl]-2-naphthoic acid,
the methyl ester of 6-[3-(tert-butyl)-4-methoxyphenyl]-2-naphthoic acid,
6-[3-(tert-butyl)-4-methoxyphenyl]-2-naphthoic acid,
the methyl ester of 6-[3-(1,1-dimethyldecyl)-4-methoxyphenyl]-2-naphthoic acid,
6-[3-(1,1-dimethyldecyl)-4-methoxyphenyl]-2-naphthoic acid.

The present invention thus features compositions comprising, formulated into the same physiologically acceptable medium:
at least one naphthoic acid compound,
benzoyl peroxide, and
at least one gelling agent of the family of the carrageenans.
The naphthoic acid is a compound of formula:

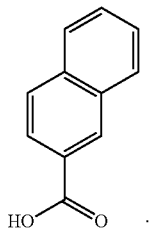

The term "naphthoic acid compound" means the compounds of formula (I):

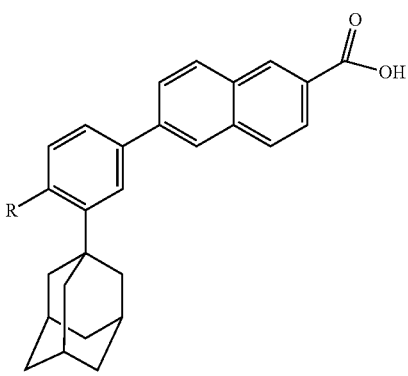

wherein
R is a hydrogen atom, a hydroxyl radical, a branched or unbranched alkyl radical having from 1 to 4 carbon atoms, an alkoxy radical having from 1 to 10 carbon atoms or a cycloaliphatic radical which is substituted or unsubstituted.

The term "linear or branched alkyl radical having from 1 to 4 carbon atoms" means the methyl, ethyl, propyl and butyl radicals.

The term "alkoxy radical having from 1 to 10 carbon atoms" is preferably understood to mean the methoxy, ethoxy, propoxy, butoxy, hexyloxy and decyloxy radicals.

The term "cycloaliphatic radical" is preferably understood to mean mono- or polycyclic radicals, such as the 1-methylcyclohexyl radical or the 1-adamantyl radical.

The selection will advantageously be made, among the naphthoic acid compounds suitable for inclusion in the compositions according to the invention, of 6-[3-(1-adamantyl)-4-methoxyphenyl]-2-naphthoic acid (adapalene), 6-[3-(1-adamantyl)-4-hydroxyphenyl]-2-naphthoic acid, 6-[3-(1-adamantyl)-4-decyloxyphenyl]-2-naphthoic acid and 6-[3-(1-adamantyl)-4-hexyloxyphenyl]-2-naphthoic acid.

The abovementioned naphthoic acid compounds are generally provided in a dispersed form in the composition according to the invention. Insoluble naphthoic acid compounds are thus homogeneously distributed in the composition according to the invention.

In particular, preference will be given to adapalene and its salts.

The term "salts of adapalene" means the salts formed with a pharmaceutically acceptable base, in particular inorganic bases, such as sodium hydroxide, potassium hydroxide and aqueous ammonia, or organic bases, such as lysine, arginine or N-methylglucamine.

The term "salts of adapalene" is also understood to mean the salts formed with fatty amines, such as dioctylamine and stearylamine.

Other retinoids can be selected from tretinoin, isotretinoin, retinoic acid, retinal, retinol or retinyl palmitate, in particular those described in the following patents or patent applications: U.S. Pat. Nos. 4,666,941, 4,581,380, EP-0210929, EP-0232199, EP-0260162, EP-0292348, EP-0325540, EP-0359621, EP-0409728, EP-0409740, EP-0552282, EP-0584191, EP-0514264, EP-0514269, EP-0661260, EP-0661258, EP-0658553, EP-0679628, EP-0679631, EP-0679630, EP-0708100, EP-0709382, EP-0722928, EP-0728739, EP-0732328, EP-0740937, EP-0776885, EP-0776881, EP-0823903, EP-0832057, EP-0832081, EP-0816352, EP-0826657, EP-0874626, EP-0934295, EP-0915823, EP-0882033, EP-0850909, EP-0879814, EP-0952974, EP-0905118, EP-0947496, WO98/56783, WO99/10322, WO99/50239 and WO99/65872.

Of course, the amount of the two active agents, benzoyl peroxide and retinoid, in the composition according to the invention would depend on the combination selected and thus in particular on the retinoid under consideration and on the quality of the desired treatment.

The preferred concentrations of retinoid are from 0.0001 to 20% by weight, with respect to the total weight of the composition.

In the compositions according to the invention, the naphthoic acid compounds are included at concentrations of less than or equal to 10% by weight, with respect to the total weight of the composition, and preferably from 0.001 to 10% by weight, with respect to the total weight of the composition, and preferably from 0.01 to 5% by weight, more preferably from 0.05 to 2% by weight and most preferably from 0.1 to 0.3% by weight, with respect to the total weight of the composition.

Throughout the present text, unless otherwise specified, it is understood that, when ranges of concentrations are given, they include the upper and lower limits of the said range.

Advantageously, the naphthoic acid compound formulated in the compositions according to the invention is 6-[3-(1-adamantyl)-4-methoxyphenyl]-2-naphthoic acid (adapalene). Preferably, in the case of adapalene, the compositions according to the invention comprise from 0.001 to 5% by weight and advantageously from 0.01 to 1% by weight of adapalene, with respect to the total weight of the composition, preferentially from 0.01 to 0.5% by weight, preferably from 0.1 to 0.4% by weight of adapalene, more preferably still 0.1% by weight or 0.3% by weight of adapalene.

In the compositions according to the invention, benzoyl peroxide is formulated at concentrations ranging from 0.5 to 10% by weight, more particularly from 1 to 7% by weight and more preferably still from 2.5 to 5% by weight, with respect to the total weight of the composition.

The benzoyl peroxide can just as easily be formulated in the free form or else in an encapsulated form, in a form adsorbed on or absorbed in any porous support.

It can, for example, be benzoyl peroxide encapsulated in a polymeric system composed of porous microspheres, such as, for example, microsponges marketed under the trademark Microsponges P009A Benzoyl Peroxide by Cardinal Healthcare.

To provide an order of magnitude, the compositions according to the invention advantageously comprise from 0.0001 and 20% by weight of benzoyl peroxide and from 0.0001 to 20% by weight of retinoid, with respect to the total weight of the composition, and preferably from 0.025 to 10% by weight of benzoyl peroxide and from 0.001 to 10% by weight of retinoid respectively, with respect to the total weight of the composition.

For example, in the compositions for the treatment of acne, the benzoyl peroxide is preferably formulated at concentrations ranging from 0.5 to 10% by weight and more particularly from 1.0 to 5% by weight, with respect to the total weight of the composition; for its part, the retinoid is formulated in this type of composition at concentrations generally ranging from 0.05 to 1% by weight, with respect to the total weight of the composition.

Advantageously, the particle size of the retinoid and of the benzoyl peroxide is such that at least 80% by number of the particles and preferably at least 90% by number of the particles have a diameter of less than 25 μm and at least 99% by number of the particles have a diameter of less than 100 μm.

The compositions according to the invention additionally comprise at least one gelling agent of the family of the carrageenans.

Carrageenans are polysaccharides constituting the cell walls of various red algae (Rhodophyceae) belonging to the Gigartinacae, Hypneaceae, Furcellariaceae and Polyideaceae families. They are generally obtained by aqueous extraction starting from natural strains of the said algae. They comprise long anionic polyelectrolyte galactane chains. These linear polymers, formed of disaccharide units, are composed of two D-galactopyranose units alternatively bonded via α and β bonds. These are highly sulfated (20-50%) polysaccharides and the α-D-galactopyranosyl residues can be in the 3',6'-anhydro form.

Initially, the carrageenans were subdivided into two families according to their solubility in KCl. The fractions soluble in KCl were denoted by the prefixes "kappa" while the "lambda" terms were reserved for the insoluble fractions. Later, the classifications were based on the number and the position of sulfate groups and on the presence of the 3',6'-anhydro bridge on the β-D-galactopyranosyl residues. This resulted in the four main families: κ, λ, β, ω and ι.

Carrageenans are essentially composed of potassium, sodium, magnesium, triethanolamine and/or calcium salts and sulfate esters of polysaccharides.

Thus, carrageenans are capable of conferring a viscosity on the composition sufficient to keep the retinoid and the benzoyl peroxide in suspension, even under the influence in particular of a variation in pH due to the release of benzoic acid by the benzoyl peroxide. For the kappa and iota forms, the contribution of potassium ions or of calcium ions is necessary to ensure gelling and thus to have an impact on the viscosity. This is because the gelling mechanism exhibits two major stages (Selim Kara, "*Photon transmission study on swelling of kappa-carrageenan gels prepared in various concentrations*", *International Journal of Biological Macromolecules*, 33 (2003), 235-243) (Tommasina Coviello, "*Polysaccharide hydrogels for modified release formulations*", *Journal of Controlled Release*, 119 (2007), 5-24):

the formation of helices;
the action of the cations causes the helices to come together and brings about the formation of aggregates.

The gelling mechanism thus takes place.

The amount of carrageenan can vary to a large extent and depends in particular on the viscosity desired, on the carrageenan used and optionally on the other gelling agents present in the composition. To provide an order of magnitude, the carrageenan can be formulated at concentrations of 0.1 to 20% by weight, with respect to the total weight of the composition, and more preferably from 0.1 to 10% to preferably from 0.5 to 2%, in particular 0.5%, 1% to 2%.

The carrageenans are marketed in particular by IMCD under the Gelcarin® and Viscarin® names (for example: Gelcarin GP812N®, Gelcarin GP379NF® or Viscarin GP209NF®).

The compositions of the present invention can be provided in all the formulation forms normally used for a topical application, in particular in the form of aqueous or oily dispersions, of suspensions, of gels, which are aqueous, anhydrous or lipophilic, or of emulsions (lotions, creams or emulsifier-free creams) with a liquid, semi-solid or solid consistency obtained by dispersion of a fatty phase in an aqueous phase (O/W) or vice-versa (W/O), with or without emulsifier.

Preferably, the compositions according to the invention are provided in the form of emulsions (creams, lotions, emulsifier-free creams), of suspensions or of gels and more preferably in the form of gels and of emulsions.

One skilled in the art will take care to select the excipients constituting the compositions according to the invention in terms of the formulation form desired and such that the advantageous properties of the compositions according to the invention are respected.

The compositions of gel type according to the invention can additionally comprise in particular one or more of the following ingredients:

a) one or more additional gelling agents and/or suspending agents and/or pH-independent gelling agents,
b) optionally, a cation,
c) one or more emollients and/or humectants,
d) one or more wetting agents,
e) optionally, one or more additives.

The compositions of emulsion type (cream, lotion, emulsifier-free cream) according to the invention can additionally comprise in particular one or more of the following ingredients:

a) one or more additional gelling agents and/or suspending agents and/or pH-independent gelling agents,
b) optionally, a cation,
c) one or more emollients and/or humectants,
d) one or more wetting agents,
e) one or more lipophilic excipients composing the fatty phase,
f) optionally, one or more emulsifiers,
g) optionally, one or more additives.

The compositions according to the invention can comprise at least one additional gelling agent and/or suspending agent and/or pH-independent gelling agent other than the carrageenans. The other additional gelling agent and/or suspending agent and/or pH-independent gelling agent can in particular be selected from the group formed by celluloses and their derivatives, polysaccharide gums, silicates and gelling agents of the family of polyacrylamides, the family of acrylic polymers coupled to hydrophobic chains and the family of modified starches.

The celluloses and their derivatives include, by way of examples, the microcrystalline cellulose and sodium carboxymethyl cellulose marketed under the trademark Avicel CL-611® by FMC Biopolymer, the ethylcellulose marketed under the trademark Ethocel® by Dow Chemical, the hydroxypropylmethylcellulose marketed under the trademark Methocel E4M® by Dow Chemical, the hydroxyethylcellulose marketed under the trademark Natrosol 250HHX® by Aqualon or the carboxymethylcellulose marketed under the Blanose® name by Aqualon.

The polysaccharide gums are complex mixtures of several polysaccharides of high molecular weight obtained by exudation from certain plants. The various types of polysaccharide gums include, by way of non-limiting examples, gum arabic, gellan gum, gum tragacanth and xanthan gum, inter alia marketed by CP Kelco under the Xantural® name (for example: Xantural® 180).

The term "silicate" is understood in particular to mean clay derivatives, more specifically magnesium aluminum silicates. These compounds are marketed in particular by R.T. Vanderbilt under the Veegum® name (for example: Veegum® HV or Veegum® K).

Particularly exemplary gelling agents are of polyacrylamide type, of the sodium acryloyldimethyltaurate copolymer/isohexadecane/polysorbate 80 mixture marketed under the trademark Sepineo P600® (or Simulgel 600PHA®) by Seppic or the polyacrylamide/C13-14 isoparaffin/laureth-7 mixture, such as, for example, marketed under the trademark Sepigel 305® by Seppic.

Particularly exemplary acrylic polymers coupled to hydrophobic chains are the PEG-150/decyl/SMDI copolymer marketed under the trademark Aculyn 44® (polycondensate comprising at least, as components, a polyethylene glycol comprising 150 or 180 mol of ethylene oxide, decyl alcohol and methylenebis(4-cyclohexyl isocyanate) (SMDI), at 35% by weight in a mixture of propylene glycol (39%) and water (26%)) by Röhm & Haas.

Particularly exemplary gelling agents of the family of modified starches are the modified potato starch marketed under the trademark Structure Solanace®, or else their mixtures, by National Starch.

The amount of additional gelling agent is generally from 0.01 to 20% by weight, with respect to the total weight of the composition.

Preference is given to combinations of carrageenans with polyacrylamides, preferably the sodium acryloyldimethyltaurate copolymer/isohexadecane/polysorbate 80 mixture marketed under the trademark Simulgel 600PHA®, or of carrageenans with celluloses and their derivatives, preferably hydroxyethylcellulose marketed under the trademark Natrosol 250HHX®, or of carrageenans with polysaccharide gums.

According to a specific embodiment, the composition can comprise a carrageenan in combination with at least one polyacrylamide and at least one cellulose gelling agent and its derivatives.

The amount of polyacrylamide can vary to a large extent and depends in particular on the viscosity desired, on the carrageenan used and optionally on the other gelling agent and/or agents present in the composition. To provide an order of magnitude, Simulgel 600PHA can be present in the composition according to the invention in amounts of from 0.01 to 10% by weight, preferably ranging from 0.05 to 6% by weight, with respect to the total weight of the composition. Advantageously, the amount is from 2 to 3%, such as, for example, 2% or 3%, with respect to the total weight of the composition.

The amount of polysaccharide gum can vary to a large extent and depends in particular on the viscosity desired, on the carrageenan used and optionally on the other gelling agent and/or agents present in the composition. To provide an order of magnitude, xanthan gum can be present in the composition according to the invention in amounts of from 0.01 to 5% by weight, preferably ranging from 0.05 to 2% by weight, with respect to the total weight of the composition. Advantageously, the amount is from 0.1 to 1%, such as, for example, 0.2% or 0.5%, with respect to the total weight of the composition.

The amount of cellulose gelling agent can vary to a large extent and depends in particular on the viscosity desired, on the carrageenan used and optionally on the other gelling agent and/or agents present in the composition. To provide an order of magnitude, the cellulose gelling agent can be present in the compositions according to the invention in amounts of from 0.01 to 10% by weight, preferably ranging from 0.05 to 5% by weight, with respect to the total weight of the composition. Advantageously, the amount ranges from 0.5 to 2%, such as, for example, 0.5%, with respect to the total weight of the composition.

The composition can comprise at least one cation, the role of which is to ensure the gelling and thus to have an impact of the viscosity of the formulation. Exemplary thereof are potassium ions and calcium ions, marketed in particular under the trademark calcium chloride dihydrate by Sigma Aldrich.

The cation which is particularly preferred is calcium.

The amount of cation can vary to a large extent and depends in particular on the viscosity desired, on the type of cation used, on the gelling agent of the family of the carrageenans and on the additional gelling agents present in the composition. To provide an order of magnitude, the cation can be included at concentrations of 0 to 10% by weight, preferably ranging from 0.001 to 8% by weight, with respect to the total weight of the composition. Advantageously, the amount is from 0.05 to 0.2%, such as, for example, 0.05%, 0.1% to 0.2%, with respect to the total weight of the composition.

The compositions can comprise one or more humectants and/or emollients. Exemplary are glycerol and sorbitol, sugars (by way of examples, glucose or lactose), polyethylene glycols (by way of example, Lutrol E400), urea or amino acids (by way of examples, serine, citrulline, arginine, asparagine or alanine).

The humectant and/or emollient which is particularly preferred is glycerol.

Exemplary wetting agents, the role of which is to reduce the surface tension and to make possible greater spreading of the liquid, without this list being limiting, are wetting agents which can preferably exhibit an HLB of 10 to 14, compounds of the family of the Poloxamers, more particularly Synperonic PE/L44 and/or Synperonic PE/L62, and/or compounds of the family of the glycols, such as propylene glycol, dipropylene glycol, lauroglycol, propylene glycol dipelargonate or ethoxydiglycol. Preferably, the wetting agents are in the liquid form, so as to be easily incorporated in the composition without it being necessary to heat it.

The wetting agent which is particularly preferred is propylene glycol and Synperonic PE/L44, marketed by Uniqema.

The compositions according to the invention can optionally comprise one or more emulsifiers.

Emulsifiers are amphiphilic compounds which have a hydrophobic moiety having an affinity for the oil and a hydrophilic moiety having an affinity for the water, thus creating a connection from the two phases. Ionic or nonionic emulsifiers thus stabilize oil/water emulsions by being adsorbed at the interface and by forming lamellar layers of liquid crystals.

The emulsifying power of nonionic emulsifiers is closely related to the polarity of the molecule. This polarity is defined by the HLB (Hydrophilic/Lipophilic Balance).

A high HLB indicates that the hydrophilic fraction is predominant and, conversely, a low HLB indicates that the lipophilic part is predominant. For example, HLB values of greater than approximately 10 correspond to hydrophilic surfactants.

Emulsifiers can be categorized, according to their structure, under the generic terms "ionic" (anionic, cationic, amphoteric) or "nonionic". Nonionic emulsifiers are emulsifiers which do not dissociate into ions in water and are thus insensitive to pH variations.

Exemplary nonionic emulsifiers exhibiting a high HLB are sorbitan esters, such as POE(20) sorbitan monooleate, marketed under the trademark Tween 80® (HLB=15); POE(20) sorbitan monostearate, marketed under the trademark Tween 60® (HLB=14.9); fatty alcohol ethers, such as POE(21) stearyl ether (HLB=15.5), marketed under the trademark Brij 721® by Uniqema, or ceteareth-20, marketed under the trademark Eumulgin B2® (HLB of 15.5) by Cognis, polyoxyethylene glycol esters, such as glyceryl stearate and PEG 100 stearate, marketed under the trademark Arlacel 165 FL® (HLB=11) by Uniqema, or PEG 6 stearate and PEG 32 stearate, marketed under the trademark Tefose 1500® (HLB=10) by Gattefossé, sucrose esters with a high HLB, such as PEG 20 methyl glucose sesquistearate, marketed under the trademark glucamate SSE20® (HLB=15) by Amerchol, sucrose laurate, marketed under the trademarks of Surfhope C-1216® (HLB=16) and Surfhope SE Pharma D-1216® by Gattefossé, sucrose stearate, marketed under the trademarks of Surfhope C-1811® (HLB=11), Surfhope SE Pharma D1811® (HLB=11) and Surfhope SE Pharma D1816® (HLB=16) by Gattefossé, sucrose palmitate/stearate, marketed under the trademark Surfhope SE Pharma D-1616® by Gattefossé, or polyglycerol esters. Preferably, the said nonionic emulsifiers with a high HLB exhibit an HLB of from 10 and 18.

Exemplary nonionic emulsifiers with a low HLB (lipophilic emulsifiers) are sorbitan esters, such as sorbitan monostearate (HLB=4.7), marketed under the trademark Span 60 by Uniqema, glycerol esters, such as glycerol monostearate, marketed under the trademark Cutina GMS-VPH (HLB=3.8) by Cognis, polyethylene glycol esters, such as PEG-6 isostearate, marketed under the trademark Olepal Isostearique® (HLB=8) by Gattefossé, or sucrose esters with a low HLB, such as methyl glucose sesquistearate, marketed under the trademark Glucate SS® (HLB=6) by Amerchol, sucrose dilaurate, marketed under the trademark Surfhope C-1205® (HLB=5), and sucrose tristearate, marketed under the trademark Surfhope C-1803® (HLB=3) and Surfhope Pharma D-1803® (HLB-3) by Gattefossé.

Other nonionic emulsifying agents are self-emulsifying waxes which make it possible to easily obtain stable emulsions by simple dispersing under hot conditions. By way of examples, cetearyl alcohol (and) polysorbate 60, marketed under the trademark Polawax NF by Croda, or Polawax GP200, marketed by Croda.

Preferred emulsifying systems are one or more "nonionic emulsifier with a high HLB"/"nonionic emulsifier with a low HLB" pairs; the system can in particular be a nonionic emulsifying system comprising at least one nonionic emulsifier exhibiting an HLB of greater than approximately 10 and at least one nonionic emulsifier exhibiting an HLB of less than approximately 10.

The ratio of each of the two emulsifiers forming the above-mentioned pair is generally determined by the calculation of the HLB required for the fatty phase provided.

Exemplary preferred emulsifiers are:

hydrophilic emulsifiers of the following types: glyceryl stearate & PEG-100 stearate, marketed under the trademark Arlacel 165FL® by Uniqema, PEG 6 stearate and PEG 32 stearate, marketed under the trademark Tefose 1500® by Gattefossé, PEG 20 methyl glucose sesquistearate, marketed under the trademark Glucamate SSE 20® by Amerchol, sucrose laurate, marketed under the trademark Surfhope SE Pharma D-1216® by Gattefossé, sucrose stearate, marketed under the trademark Surfhope SE Pharma D1816® by Gattefossé, sucrose palmitate/stearate, marketed under the trademark Surfhope SE Pharma D-1616® by Gattefossé, polyoxyethylene (21) stearyl ether, marketed under the trademark Brij721® by Uniqema, ceteareth-20, marketed under the trademark Eumulgin B2PH® by Cognis, or sorbitan esters, marketed under the trademarks of Tween 80® and Tween 60®;

lipophilic emulsifiers of methyl glucose sesquistearate type, such as Glucate SS®, marketed by Amerchol, sucrose dilaurate, such as Surfhope C-1205®, marketed by Gattefossé, and sucrose tristearate, such as Surfhope D-1803®, marketed by Gattefossé.

The compositions according to the invention can also comprise a fatty phase. This fatty phase can comprise, for example, vegetable, mineral, animal or synthetic oils, silicone oils and their mixtures.

Exemplary mineral oils are liquid paraffins with different viscosities, such as Primol 352®, Marcol 82® or Marcol 152®, which are marketed by Esso.

Exemplary vegetable oils or its substitute of vegetable origin are sweet almond oil, palm oil, soyabean oil, sesame oil or sunflower oil.

Exemplary animal oils are lanolin, squalene or fish oil, with, as derivative, perhydrosqualene, marketed under the trademark Sophiderm® by Sophim.

Exemplary synthetic oils are an ester, such as cetearyl isononanoate, for example the product marketed under the trademark Cetiol SN PH® by Cognis France, diisopropyl adipate, such as the product marketed under the trademark Crodamol DA® by Croda, isopropyl palmitate, such as the product marketed under the trademark Crodamol IPP® by Croda, or caprylic/capric triglyceride, such as Miglyol 812®, marketed by Univar.

Exemplary silicone oils are a dimethicone, such as the product marketed under the trademark Q7-9120 Silicone Fluid®, with a viscosity of 20 cSt to 12500 cSt, by Dow Corning, or of a cyclomethicone, such as the product marketed under the trademark ST-Cyclomethicone 5NF®, also by Dow Corning.

Exemplary hydrogenated polyisobutenes are the Parleam® products marketed by Rossow.

An exemplary Guerbet alcohol is octyldodecanol, marketed under the trademark Eutanol G by Cognis.

Also included may be solid fatty substances, such as natural or synthetic waxes, fatty acids, such as stearic acid, fatty alcohols, such as the Speziol C18 Pharma marketed by Cognis, texturing agents of tribehenate type, such as Compritol 888, marketed by Gattefossé, or hydrogenated castor oils, such as Cutina HR, marketed by Cognis. In this case, one skilled in the art will adjust the heating temperature of the preparation according to the presence or absence of these solids.

For the composition according to the invention, the silicone oil and more particularly ST-Cyclomethicone 5NF® is preferred.

The compositions can optionally comprise any additive conventionally employed in the cosmetics or pharmaceutical field, such as antioxidants, sunscreens, preservatives (by way of examples, benzalkonium chloride, phenoxyethanol, benzyl alcohol, diazolidinylurea, parabens or their mixtures), fillers, electrolytes, colorants, an agent which stabilizes benzoyl peroxide (by way of examples, sodium docusate, sodium C14-16 olefin sulfonate, lactic acid or citric acid), neutralizing agents of normal inorganic or organic base or acid type (by way of examples, triethanolamine, 10% sodium hydroxide solution, citric acid/sodium citrate buffer or succinic acid/sodium succinate buffer), fragrances, essential oils, cosmetic active principles, moisturizing agents, vitamins, essential fatty acids, sphingolipids, self-tanning compounds, such as DHA, or soothing and protective agents for the skin, such as allantoin.

Of course, one skilled in the art will take care to select this or these optional additional compound or compounds and/or their amounts in such a way that the advantageous properties of the composition according to the invention are not, or not substantially, detrimentally affected.

These additives can be present in the composition at a content of from 0 to 20% by weight, with respect to the total weight of the composition, preferably of from 0 to 10% by weight.

The aqueous phase according to the invention can comprise water, a floral water, such as cornflower water, or a natural thermal or mineral water, such as, for example, water from Vittel.

The said aqueous phase can be present at a content of from 10 to 95% by weight, with respect to the total weight of the composition, preferably of from 20 to 90% by weight.

In particular, this invention also features a pharmaceutical or cosmetic compositions for topical application to the skin, superficial body growths or mucous membranes in the form of an aqueous gel, which comprise, formulated into a physiologically acceptable medium compatible with topical application to the skin, superficial body growths or mucous membranes (expressed as percentage by weight):
  from 20 to 90% of water;
  from 0.01 to 10%, preferably from 0.1 to 8%, of wetting agents;
  from 0.0001 to 20%, preferably from 0.025 to 10%, of benzoyl peroxide;
  from 0.0001 to 20%, preferably from 0.001 to 10%, of retinoid;
  from 0.1 to 20%, preferably from 0.1 to 10%, of carrageenans;
  from 0 to 10%, preferably from 0.05 to 0.2%, of cations;
  from 0.01 to 15%, preferably from 0.05 to 10%, of one or more humectants and/or emollients;
  from 0.01 to 10%, preferably from 0.05 to 6%, of additional gelling agent and/or suspending agent and/or pH-independent gelling agent;
  from 0 to 20%, preferably from 0 to 10%, of additives.

In particular, this invention also features pharmaceutical or cosmetic compositions for topical application to the skin, superficial body growths or mucous membranes in the form of an emulsion, which comprise, formulated into a physiologically acceptable medium compatible with topical application to the skin, superficial body growths or mucous membranes (expressed as percentage by weight):
  from 20 to 90% of water;
  from 0.01 to 10%, preferably from 0.1 to 8%, of wetting agents;
  from 0.0001 to 20%, preferably from 0.025 to 10%, of benzoyl peroxide;
  from 0.0001 to 20%, preferably from 0.001 to 10%, of retinoid;
  from 0.1 to 20%, preferably from 0.1 to 10%, of carrageenans;
  from 0 to 10%, preferably from 0.05 to 0.2%, of cations;
  from 0.01 to 15%, preferably from 0.05 to 10%, of one or more humectants and/or emollients;
  from 0.01 to 10%, preferably from 0.05 to 6%, of additional gelling agent and/or suspending agent and/or pH-independent gelling agent;
  from 0 to 15%, preferably from 0 to 10%, of emulsifiers;
  from 0 to 20%, preferably from 0 to 10%, of additives.

The methodology for the formulation of the compositions according to the invention includes conventional methods which can be optionally adjusted by one skilled in the art.

The main process for the formulation of the compositions according to the invention comprises, by way of example, the following stages:

Stage a: Preparation of Active Phase 1:

Purified water and active principle 1 (adapalene) are mixed with at least one wetting agent until the said naphthoic acid compound is completely dispersed, to obtain active phase 1.

Stage b: Preparation of Active Phase 2:

Purified water and active principle 2 (benzoyl peroxide) are mixed with at least one wetting agent until the said benzoyl peroxide has completely dispersed, to obtain active phase 2.

Stage c: Preparation of the Aqueous Phase:

Purified water, the gelling agent of the family of the carrageenans, the additional gelling agent or agents and/or suspending agent or agents and/or pH-independent gelling agent or agents (with the exception of the polyacrylamide), the cation, the humectant or humectants and/or emollient or emollients and optionally the preservative or preservatives and the hydrophilic emulsifier or emulsifiers are introduced with stirring into a beaker, if necessary under hot conditions.

Stage d: Mixing of the Active Phases:

The two active phases obtained in a) and b) respectively are mixed. Stirring is maintained until the mixture is completely homogeneous.

Stage e (Optionally to Obtain an Emulsion): Preparation of the Fatty Phase:

The oily compounds, the solid fatty substances and optionally the lipophilic emulsifiers and the preservatives are mixed.

The mixture is heated and, after homogenization, the volatile silicone is introduced last, if present in the composition.

Stage f (Optional): Emulsification:

The fatty phase is introduced under hot conditions into the aqueous phase, to bring about emulsification. Heating is maintained for a few minutes and then the preparation is cooled.

Stage g: Addition of the Single Active Phase:

The single active phase obtained in d) is introduced into the aqueous phase obtained in c) for the gels or into the phase obtained in f) for the emulsions.

Stage h (Optional): Addition of the Polyacrylamide:

The polyacrylamide is introduced with stirring into the phase obtained in g). Stirring is maintained until the mixture is completely homogeneous.

Stage i: Neutralization:

The agent for neutralizing the gelling agent is introduced, if necessary, into the phase obtained in stage g).

Stage j (Optional): Adjustment with Regard to Water:

If necessary, an adjustment with regard to water is carried out.

The alternative process for the formulation of a composition according to the invention comprises, by way of example, the following stages:

The active principles are mixed in the 1st stage of the process described above; thus, stages a) and b) are replaced by stage a'):

a') Preparation of the Single Active Phase Comprising the Two Active Principles.

The process is subsequently continued as described starting from stage c), with elimination of stage d).

In more detail, the main process for the formulation of a composition according to the invention comprises the following stages:

Stage a: Preparation of Active Phase 1:

Purified water, the active principle (adapalene) and the wetting agents (type Synperonic PE/L62, Synperonic PE/L44, propylene glycol) are introduced with stirring into a beaker. The mixture is maintained under stirring until completely dispersed.

Stage b: Preparation of Active Phase 2:

Purified water, the active principle (benzoyl peroxide) and the wetting agents (type Synperonic PE/L62, Synperonic PE/L44, propylene glycol) are introduced with stirring into a beaker. The mixture is maintained under stirring until completely dispersed.

Stage c: Preparation of the Aqueous Phase:

Purified water, the gelling agent of the family of the carrageenans (type Gelcarin GP379NF), the additional gelling agent or agents (type Xantural 180, Natrosol 250HHX) and/or suspending agents (type Avicel CL-611) and/or pH-independent gelling agents (with the exception of the Simulgel 600PHA), the cation, the emollient or emollients and/or humectant or humectants (type glycerol) and optionally the preservative or preservatives (type methylparaben) and the hydrophilic emulsifiers (type Tween 80) are introduced with stirring into a beaker, if necessary under hot conditions.

Stage d: Mixing the Active Phases:

The two active phases obtained in a) and b) respectively are mixed. Stirring is maintained until completely homogeneous.

Stage e (Optional): Preparation of the Fatty Phase:

The oils and solid fatty substances (type olepal isostearique, Cetiol SN PH, Crodamol DA, Speziol C18 and Cosbiol) and optionally the emulsifiers (type Glucate SS, Glucamate SSE 20, Brij 721 and Tefose 1500) and preservatives (type phenoxyethanol and propylparaben) are mixed.

The mixture is heated and, after homogenization, the volatile silicone (type Cyclomethicone 5NF) is introduced, if the latter is present in the composition.

Stage f (Optional): Emulsification:

The fatty phase is introduced into the aqueous phase under hot conditions to carry out emulsification. Heating is maintained for a few minutes and then the preparation is cooled.

Stage g: Addition of the Single Active Phase:

The single active phase obtained in e) is introduced into the aqueous phase obtained in c) for the gels or into the phase obtained in f) for the emulsions.

Stage h (Optional): Addition of the Simulgel 600PHA:

The Simulgel 600PHA is introduced with stirring into the phase obtained in g). Stirring is maintained until completely homogeneous.

Stage i: Neutralization:

If necessary, the agent for neutralization of the gelling agent (type triethanolamine or 10% sodium hydroxide solution) is introduced into the phase obtained in stage g).

Stage j (Optional): Adjustment with Regard to Water:

If necessary, an adjustment with regard to water is carried out.

In more detail, the alternative process for the formulation of a composition according to the invention comprises the following stages:

The active principles are mixed in the 1st stage of the process described above; thus, stages a) and b) are replaced by stage a'):

a') Preparation of the Single Active Phase Comprising the Two Active Principles:

The naphthoic acid derivative and the benzoyl peroxide are mixed with at least one wetting agent in water until the said benzoyl peroxide and the said naphthoic acid derivative are completely dispersed, to obtain a single active phase, according to the same operating conditions.

The process is subsequently continued as described starting from stage c) and stage d) is eliminated.

The present invention also features the compositions as described above as medicaments.

This invention also features administration of the novel compositions as described above in cosmetics and in dermatology.

Due to the keratolytic, bactericidal and anti-inflammatory activity of benzoyl peroxide and the marked activity of retinoids in the fields of cell differentiation and proliferation, the compositions of the invention are particularly well suited in the following therapeutic fields:

1) for treating dermatological conditions and afflictions linked to a disorder of keratinization involving differentiation and proliferation, in particular for treating acne vulgaris, comedonic or polymorphic acne, acne rosacea, nodulocystic acne, acne conglobata, senile acne, secondary acnes, such as solar, drug or occupational acne, or hidradenitis suppurativa, 2) for treating other types of disorders of keratinization, in particular ichthyoses, ichthyosiform conditions, Darier's disease, palmoplantar keratoderma, leukoplakia and leucoplakiform conditions, or cutaneous or mucosal (oral) lichen, 3) for treating other dermatological conditions linked to a disorder of keratinization with an inflammatory and/or immunoallergic component and, in particular, all forms of psoriasis, whether cutaneous, mucosal or ungual, and even psoriatic rheumatism, or alternatively cutaneous atopy, such as eczema, or respiratory atopy or alternatively gingival hypertrophy; the compounds can also be used in some inflammatory conditions not exhibiting disorder of keratinization, such as folliculitis, 4) for treating all dermal or epidermal proliferations, whether they are benign or malignant and whether they are or are not of viral origin, such as common warts, flat warts, molluscum contagiosum and epidermodysplasia verruciformis, florid or oral papillomatoses, and the proliferations which can be induced by ultraviolet radiation, in particular in the case of actinic keratoses, 5) for repairing or combating skin aging, whether photoinduced or chronologic, or for reducing pigmentations, or any pathology associated with chronologic or actinic aging;

6) for preventively or curatively treating disorders of cicatrization or skin ulcers, for preventing or repairing stretch marks, or alternatively for promoting cicatrization, 7) for combating disorders of the sebaceous function, such as hyperseborrhoea of acne or simple seborrhoea, 8) in the treatment of any condition of fungal origin on the skin, such as tinea pedis and tinea versicolor, 9) in the treatment of dermatological conditions with an immunological component, 10) in the treatment of skin disorders due to exposure to UV radiation.

The compositions according to the invention are particularly useful for the preventive or curative treatment of acne vulgaris.

This invention also features manufacture of a pharmaceutical preparation useful for the prevention or treatment of dermatological conditions and afflictions linked to disorders of cell differentiation and/or proliferation and/or of keratinization, as well as the manufacture of a pharmaceutical preparation intended to prevent or treat acne vulgaris.

The compositions according to the invention are also useful in the cosmetics field, in particular for the treatment of skin with a tendency towards acne, for hair growth, for combating hair loss, for combating the greasy appearance of the skin or hair, in protecting against the harmful effects of the sun or in treating physiologically greasy skin, or for preventing and/or for combating photoinduced or chronologic aging.

The compositions according to the invention are also useful in body and hair hygiene.

The present invention thus also features the cosmetic application of a subject composition for the treatment of skin with a tendency towards acne, for causing hair growth or preventing hair loss, for combating the greasy appearance of the skin or hair, in protecting against the harmful effects of the sun or in treating physiologically greasy skin, or for preventing and/ or for combating photoinduced or chronologic aging.

The present invention will now be illustrated by the physical and chemical stability data presented below.

The physical stability of the formulations is monitored by macroscopic and microscopic observation of the formulation stored at ambient temperature at T0, T+1 month, T+2 months and T+3 months.

At AT, macroscopic observation makes it possible to guarantee the physical integrity of the products.

Microscopic observation makes it possible to evaluate the quality of the dispersion of the two active principles. The adapalene is observed in fluorescent light while the benzoyl peroxide is observed in polarized light.

The characterization of the finished product is completed by a measurement of the yield point and of the viscosity.

A Haake rheometer of VT550 type with an SVDIN measurement spindle was used for the measurement of the yield point.

The rheograms are recorded at 25° C. and under a controlled rate from 0 to 100 s$^{-1}$. The viscosity values are given at the shear values of 4 s$^{-1}$, 20 s$^{-1}$ and 100 s$^{-1}$ ($\gamma$). The term "yield point" ($\tau_0$, expressed in pascals) means the force necessary (minimum shear stress) to overcome the cohesive forces of Van der Waals type and to bring about flow.

Viscometers of Brookfield RVDVII+ and LDVDII+ type are used for the viscosity measurements.

The viscosity ranges which can be measured with the two types of Brookfield viscometer are as follows:

RVDVII+ viscometer: 100 cP-40 McP
LVDVII+ viscometer: 15 cP-6 McP

For the emulsions, at the starting moment T0:
a cream is regarded as present if the viscosity is greater than 30,000 cP, a lotion is regarded as present if the viscosity is less than 30,000 cP (Lucinda Buhse, ACPS, Oct. 22, 2003, Pharmaceutical Nomenclature—Issues and Challenges).

The chemical stability of the adapalene and the benzoyl peroxide is assayed by HPLC.

The results are expressed as mg/g of adapalene and of benzoyl peroxide and as % with respect to the theoretical content.

To further illustrate the present invention and the advantages thereof, the following specific examples are given, it being understood that same are intended only as illustrative and in nowise limitative. In said examples to follow, all parts and percentages are given by weight, unless otherwise indicated.

Example 1

Formulation of Gel Type Comprising 2.5% Benzoyl Peroxide and 0.1% Adapalene

| Example 1 | |
|---|---|
| Water | q.s. 100% |
| Adapalene | 0.1% |
| Benzoyl peroxide (in the microsponge form) | q.s. 2.5% BPO |
| Propylene glycol | 4% |
| Poloxamer 124 | 0.2% |
| Disodium EDTA | 0.1% |
| Solagum LP | 2% |
| Xanthan gum (Xantural 180) | 0.2% |
| Glycerol | 4% |
| Sodium docusate | 0.05% |

Example 2

Formulation of Gel Type Comprising 2.5% Benzoyl Peroxide, 0.1% Adapalene and 0.5% Gelcarin GP 379NF as Gelling Agent of the Family of the Carrageenans

| Example 2 | |
|---|---|
| Water | q.s. 100% |
| Adapalene | 0.1% |
| Benzoyl peroxide | 2.5% |
| Propylene glycol | 4.0% |
| Synperonic PE/L44 | 0.2% |
| Glycerol | 4.0% |
| Gelcarin GP379NF | 0.5% |
| Calcium chloride dihydrate | 0.05% |
| Simulgel 600PHA | 3.0% |

Stability Data:
Physical Stability:

| Characterization at T0 | | |
|---|---|---|
| | Macroscopic appearance | White gel |
| | Microscopic appearance | Dispersion of the active principles without aggregates >100 µm |
| | pH | 5.45 |
| Viscosity data | Haake (4 s$^{-1}$/20 s$^{-1}$/ 100 s$^{-1}$) | 93/129/185 |
| | Brookfield RVDVII+ (S29; 5 rpm) | 66560 cP |

|  |  | T+1 month | T+2 months | T+3 months |
|---|---|---|---|---|
| Macroscopic appearance | AT | Identical to T0 | Identical to T0 | Identical to T0 |
| Microscopic appearance | AT | Identical to T0 | Identical to T0 | Identical to T0 |
| pH | AT | 4.87 | 4.80 | 4.34 |
| Haake rheology ($4\,s^{-1}/20\,s^{-1}/100\,s^{-1}$) |  | 104/144/200 | 99/135/197 | 97/139/196 |
| Brookfield RVDVII+ (S29; 5 rpm) |  | 71800 cP | 69400 cP | 73800 cP |

Chemical Stability:

Adapalene:

|  |  | Time | | | |
|---|---|---|---|---|---|
| Stability conditions |  | T0 | T + 1 month | T + 2 months | T + 3 months |
| AT | mg/g | 0.93 | 0.91 | 0.94 | 0.92 |
|  | % of the theoretical content | 93 | 91 | 94 | 92 |

Benzoyl Peroxide:

|  |  | Time | | | |
|---|---|---|---|---|---|
| Stability conditions |  | T0 | T + 1 month | T + 2 months | T + 3 months |
| AT | mg/g | 23.30 | 23.46 | 23.38 | 23.34 |
|  | % of the theoretical content | 93 | 94 | 94 | 93 |

Example 3

Formulation of Gel Type Comprising 2.5% Benzoyl Peroxide, 0.1% Adapalene and 0.50% Gelcarin GP 379NF as Gelling Agent of the Family of the Carrageenans

| Example 3 | |
|---|---|
| Water | q.s. 100% |
| Adapalene | 0.1% |
| Benzoyl peroxide | 2.5% |
| Propylene glycol | 4.0% |
| Synperonic PE/L44 | 0.2% |
| Glycerol | 4.0% |
| Gelcarin GP379NF | 0.50% |
| Calcium chloride dihydrate | 0.05% |
| Simulgel 600PHA | 2.0% |
| Natrosol 250HHX | 0.5% |

Stability Data:

Physical Stability:

| Characterization at T0 | | |
|---|---|---|
| Macroscopic appearance | | White gel |
| Microscopic appearance | | Dispersion of the active principles without aggregates >100 μm |
| Viscosity data | pH | 6.24 |
|  | Haake ($4\,s^{-1}/20\,s^{-1}/100\,s^{-1}$) | 185/237/300 |
|  | Brookfield RVDVII+ (S29; 5 rpm) | $130 \times 10^3$ cP |

|  |  | T+1 month | T+2 months | T+3 months |
|---|---|---|---|---|
| Macroscopic appearance | AT | Identical to T0 | Identical to T0 | Identical to T0 |
| Microscopic appearance | AT | Identical to T0 | Identical to T0 | Identical to T0 |
| pH | AT | 4.92 | 4.66 | 4.26 |
| Haake rheology ($4\,s^{-1}/20\,s^{-1}/100\,s^{-1}$) |  | 190/254/321 | 170/216/261 | 178/248/327 |
| Brookfield RVDVII+ (S29; 5 rpm) |  | $134 \times 10^3$ cP | $133 \times 10^3$ cP | $136 \times 10^3$ cP |

Chemical Stability:

Adapalene:

|  |  | Time | | | |
|---|---|---|---|---|---|
| Stability conditions |  | T0 | T + 1 month | T + 2 months | T + 3 months |
| AT | mg/g | 0.98 | 0.98 | 1.00 | 1.01 |
|  | % of the theoretical content | 98 | 98 | 100 | 101 |

Benzoyl Peroxide:

| Stability conditions | Time | T0 | T+1 month |
|---|---|---|---|
| AT | mg/g | 22.79 | 24.62 |
|  | % of the theoretical content | 91 | 99 |

Example 4

Formulation of lotion type comprising 1.0% Benzoyl Peroxide, 0.3% Adapalene and 2.00% Gelcarin GP 379NF as Gelling Agent of the Family of the Carrageenans

| Example 4 | |
|---|---|
| Water | q.s. 100% |
| Adapalene | 0.3% |
| Benzoyl peroxide | 1.0% |

-continued

| Example 4 | |
|---|---|
| Dipropylene glycol | 3.0% |
| Synperonic PE/L44 | 0.2% |
| Glycerol | 4.0% |
| Gelcarin GP379NF | 2.0% |
| Calcium chloride dihydrate | 0.2% |
| Simulgel 600PHA | 2.0% |
| Cetiol SN PH | 5.0% |
| Perhydrosqualene | 5.0% |
| Nipasol M | 0.05% |
| Arlacel 165FL | 3.0% |
| Brij 721 | 3.0% |

Stability Data:

Physical Stability:

| Characterization at T0 | | |
|---|---|---|
| Macroscopic appearance | | White lotion |
| Microscopic appearance | | Dispersion of the active principles without aggregates >100 μm |
| | pH | 6.21 |
| Viscosity data | Haake ($4\,s^{-1}/20\,s^{-1}/100\,s^{-1}$) | 49/89/185 |
| | Brookfield LVDVII+ (S64; 10 rpm) | 29814 cP |

| | | T+1 month | T+2 months | T+3 months |
|---|---|---|---|---|
| Macroscopic appearance | AT | Identical to T0 | Identical to T0 | Identical to T0 |
| Microscopic appearance | AT | Identical to T0 | Identical to T0 | Identical to T0 |
| pH | AT | 6.12 | 5.47 | 4.89 |
| Haake rheology ($4\,s^{-1}/20\,s^{-1}/100\,s^{-1}$) | | 38/73/170 | 42/80/172 | 43/83/171 |
| Brookfield LVDVII+ (S64; 10 rpm) | | 28254 cP | 31073 cP | 28194 cP |

Chemical Stability:

Adapalene:

| | | | Time | | |
|---|---|---|---|---|---|
| Stability conditions | | T0 | T + 1 month | T + 2 months | T + 3 months |
| AT | mg/g | 2.87 | 2.90 | 2.85 | 2.93 |
| | % of the theoretical content | 96 | 97 | 95 | 98 |

Benzoyl Peroxide:

| | | | Time | | |
|---|---|---|---|---|---|
| Stability conditions | | T0 | T + 1 month | T + 2 months | T + 3 months |
| AT | mg/g | 9.50 | 9.69 | 9.57 | 9.52 |
| | % of the theoretical content | 95 | 97 | 96 | 95 |

Example 5

Formulation of Cream Type Comprising 2.5% Benzoyl Peroxide, 0.1% Adapalene and 1.00% Gelcarin GP 379NF as Gelling Agent of the Family of the Carrageenans

| Example 5 | |
|---|---|
| Water | q.s. 100% |
| Adapalene | 0.1% |
| Benzoyl peroxide | 2.5% |
| Propylene glycol | 6.0% |
| Synperonic PE/L44 | 0.2% |
| Glycerol | 7.0% |
| Gelcarin GP379NF | 1.0% |
| Calcium chloride dihydrate | 0.1% |
| Simulgel 600PHA | 2.0% |
| Eumulgin B2PH | 3.0% |
| Speziol C18 Pharma | 2.0% |
| Miglyol 812N | 7.0% |
| ST-Cyclomethicone 5NF | 6.0% |
| Arlacel 165FL | 3.0% |

Stability Data:

Physical Stability:

| Characterization at T0 | | |
|---|---|---|
| Macroscopic appearance | | White cream |
| Microscopic appearance | | Dispersion of the active principles without aggregates >100 μM |
| | pH | 6.33 |
| Viscosity data | Haake ($4\,s^{-1}/20\,s^{-1}/100\,s^{-1}$) | 101/137/220 |
| | Brookfield RVDVII+ (S34; 5 rpm) | 80128 cP |

| | | T+1 month | T+2 months | T+3 months |
|---|---|---|---|---|
| Macroscopic appearance | AT | Identical to T0 | Identical to T0 | Identical to T0 |
| Microscopic appearance | AT | Identical to T0 | Identical to T0 | Identical to T0 |
| pH | AT | 5.80 | 4.73 | 5.00 |

-continued

|  | T+1 month | T+2 months | T+3 months |
|---|---|---|---|
| Haake rheology ($4\,s^{-1}/20\,s^{-1}/100\,s^{-1}$) | 103/139/209 | 101/136/214 | 107/146/223 |
| Brookfield RVDVII+ (S34; 5 rpm) | 81664 cP | 67200 cP | 76544 cP |

Chemical Stability:

Adapalene:

| Stability conditions | | T0 | T + 1 month | T + 2 months | T + 3 months |
|---|---|---|---|---|---|
| AT | mg/g | 0.97 | 0.97 | 0.96 | 0.98 |
|  | % of the theoretical content | 97 | 97 | 96 | 98 |

Benzoyl Peroxide:

| Stability conditions | | T0 | T + 1 month | T + 2 months | T + 3 months |
|---|---|---|---|---|---|
| AT | mg/g | 23.11 | 23.90 | 23.68 | 23.66 |
|  | % of the theoretical content | 92 | 96 | 95 | 95 |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable dermatological composition suited for treating acne, said composition comprising thus effective amounts of at least one retinoid and dispersed benzoyl peroxide, at least one iota carrageenan gelling agent, and at least one cation selected from the group consisting of potassium cations and calcium cations, formulated together in the same topically applicable, physiologically acceptable medium therefor, said composition being chemically, physically and rheologically stable for three months at ambient temperature.

2. The dermatological composition as defined by claim 1, said at least one retinoid comprising a naphthoic acid compound.

3. The dermatological composition as defined by claim 1, comprising from 0.1 to 20% by weight with respect to the total weight of the composition, of carrageenan.

4. The dermatological composition as defined by claim 1, further comprising at least one additional gelling agent.

5. The dermatological composition as defined by claim 4, said at least one additional gelling agent comprising a semi-synthetic cellulose, polysaccharide gum, silicate, acrylic polymer coupled to a hydrophobic chain, modified starch and/or polyacrylamide.

6. The dermatological composition as defined by claim 5, wherein the amount of additional gelling agent ranges from 0.01% to 20% by weight, with respect to the total weight of the composition.

7. The dermatological composition as defined by claim 1, comprising from 0.0001% to 20% of said at least one retinoid by weight, with respect to the total weight of the composition.

8. The dermatological composition as defined by claim 1, said at least one retinoid comprising adapalene.

9. The dermatological composition as defined by claim 1, comprising from 0.0001% to 20% of benzoyl peroxide by weight, with respect to the total weight of the composition.

10. The dermatological composition as defined by claim 1, wherein the benzoyl peroxide is encapsulated.

11. The dermatological composition as defined by claim 1, further comprising at least one propenetrating agent.

12. The dermatological composition as defined by claim 11, comprising from 0.01% to 20% of propenetrating agent by weight, with respect to the total weight of the composition.

13. The dermatological composition as defined by claim 9, said at least one propenetrating agent comprising propylene glycol.

14. The dermatological composition as defined by claim 1, further comprising at least one wetting liquid surfactant.

15. The dermatological composition as defined by claim 14, comprising from 0.01% to 10% of wetting liquid surfactant by weight, with respect to the total weight of the composition.

16. The dermatological composition as defined by claim 15, said at least one wetting liquid surfactant comprising a poloxamer.

17. The dermatological composition as defined by claim 1, formulated as a gel.

18. The dermatological composition as defined by claim 1, comprising (expressed as percentage by weight):
   from 20 to 90% of water;
   from 0.01 to 10% of wetting agents;
   from 0.0001 to 20% of benzoyl peroxide;
   from 0.0001 to 20% of at least one retinoid;
   from 0.1 to 20% of at least one iota carrageenan;
   from 0.001% to 10% of cations;
   from 0.01 to 15% of one or more humectants and/or emollients;
   from 0.01 to 10% of additional gelling agent and/or suspending agent and/or pH-independent gelling agent; and
   from 0 to 20% of additives.

19. The dermatological composition as defined by claim 1, formulated as an emulsion.

20. The dermatological composition as defined by claim 1, comprising (expressed as percentage by weight):
   from 20 to 90% of water;
   from 0.01 to 10% of wetting agents;
   from 0.0001 to 20% of benzoyl peroxide;
   from 0.0001 to 20% of at least one retinoid;
   from 0.1 to 20% of at least one iota carrageenan;
   from 0.001% to 10% of cations;
   from 0.01 to 15% of one or more humectants and/or emollients;
   from 0.01 to 10% of additional gelling agent and/or suspending agent and/or pH-independent gelling agent;
   from 0 to 15% of emulsifiers; and
   from 0 to 20% of additives.

21. The dermatological composition as defined by claim 1, formulated as a medicament.

22. A regime or regimen for treating acne vulgaris, comedonic or polymorphic acne, nodulocystic acne, acne conglobata, senile acne or secondary acne, comprising administering to an individual in need of such treatment, a thus effective amount of a dermatological composition as defined by claim 1.

23. A regime or regimen for treating acne vulgaris, comprising administering to an individual in need of such treatment, a thus effective amount of a dermatological composition as defined by claim 1.

24. A topically applicable dermatological composition suited for treating acne, said composition comprising thus effective amounts of at least one retinoid and dispersed benzoyl peroxide, from 0.1% to 20% by weight of at least one iota carrageenan gelling agent, and from 0.001% to 10% by weight of cations, the cations being selected from the group consisting of potassium cations and calcium cations, formulated together in the same topically applicable, physiologically acceptable medium therefor, the percents by weight being relative to the total weight of the composition, said composition being chemically, physically and rheologically stable for three months at ambient temperature.

25. The dermatological composition as defined by claim 24, wherein the amount of iota carrageenan gelling agent is from 0.1% to 10% by weight and the amount of cations is from 0.001% to 8% by weight.

26. The dermatological composition as defined by claim 25, wherein the amount of iota carrageenan gelling agent is from 0.5% to 2% by weight and the amount of cations is from 0.05% to 0.2% by weight.

27. The dermatological composition as defined by claim 26, wherein the amount of iota carrageenan gelling agent is 0.5%, 1% or 2% by weight and the amount of cations is 0.05%, 0.1% or 0.2% by weight.

28. The dermatological composition as defined by claim 1, wherein the retinoid is a naphthoic acid compound comprising from 0.001% to 10% by weight with respect to the total weight of the composition.

29. The dermatological composition as defined by claim 28, wherein the amount of naphthoic acid compound is from 0.01% to 5% by weight.

30. The dermatological composition as defined by claim 24, wherein the retinoid is a naphthoic acid compound comprising from 0.001% to 10% by weight with respect to the total weight of the composition.

31. The dermatological composition as defined by claim 30, wherein the amount of naphthoic acid compound is from 0.01% to 5% by weight.

32. The dermatological composition as defined by claim 24, wherein the retinoid is adapalene.

33. The dermatological composition as defined by claim 32, comprising from 0.001% to 5% by weight of adapalene.

34. The dermatological composition as defined by claim 33, wherein the amount of adapalene is from 0.01% to 1% by weight.

35. The dermatological composition as defined by claim 34, wherein the amount of adapalene is from 0.01% to 0.5% by weight.

36. The dermatological composition as defined by claim 35, wherein the amount of adapalene is from 0.1% to 0.4% by weight.

37. The dermatological composition as defined by claim 36, wherein the amount of adapalene is 0.1% or 0.3% by weight.

38. The dermatological composition as defined by claim 1, comprising from 0.5% to 10% by weight of benzoyl peroxide with respect to the total weight of the composition.

39. The dermatological composition as defined by claim 1, comprising from 0.025% to 10% by weight of benzoyl peroxide with respect to the total weight of the composition.

40. The dermatological composition as defined by claim 39, wherein the amount of benzoyl peroxide is from 1% to 7% by weight.

41. The dermatological composition as defined by claim 40, wherein the amount of benzoyl peroxide is from 2.5% to 5% by weight.

42. The dermatological composition as defined by claim 24, comprising from 0.5% to 10% by weight of benzoyl peroxide with respect to the total weight of the composition.

43. The dermatological composition as defined by claim 24, comprising from 0.025% to 10% by weight of benzoyl peroxide with respect to the total weight of the composition.

44. The dermatological composition as defined by claim 43, wherein the amount of benzoyl peroxide is from 1% to 7% by weight.

45. The dermatological composition as defined by claim 44, wherein the amount of benzoyl peroxide is from 2.5% to 5% by weight.

46. A topically applicable dermatological composition suited for treating acne, said composition comprising from 0.01% to 0.5% by weight of adapalene, from 1% to 7% by weight of dispersed benzoyl peroxide, from 0.1% to 10% by weight of at least one iota carrageenan gelling agent and from 0.001% to 8% by weight of cations, the cations being selected from the group consisting of potassium cations and calcium cations, formulated together in the same topically applicable, physiologically acceptable medium therefor, the percents by weight being relative to the total weight of the composition, said composition being chemically, physically and rheologically stable for three months at ambient temperature.

\* \* \* \* \*